United States Patent [19]

Spier et al.

[11] Patent Number: 4,921,490
[45] Date of Patent: May 1, 1990

[54] SAFETY HYPODERMIC NEEDLE SYRINGE

[76] Inventors: I. Martin Spier, 50 Park Ave., New York, N.Y. 10016; Martin F. Sturman, 7315 Granite Rd., Melrose Park, Pa. 19126

[21] Appl. No.: 377,275

[22] Filed: Jul. 10, 1989

Related U.S. Application Data

[63] Continuation-in-part of Ser. No. 235,466, Aug. 24, 1988, Pat. No. 4,863,435.

[51] Int. Cl.⁵ .............................................. A61M 5/32
[52] U.S. Cl. .................................... 604/192; 604/263
[58] Field of Search ................ 604/192, 198, 187, 263

[56] References Cited

U.S. PATENT DOCUMENTS 4,813,426  3/1989  Haber et al. .................... 604/198 X
4,813,940  3/1989  Parry .............................. 604/263 X
4,820,275  4/1989  Haber et al. ........................ 604/198

Primary Examiner—John D. Yasko
Attorney, Agent, or Firm—Michael Ebert

[57] ABSTRACT

A hypodermic syringe provided with a safety hypodermic needle and shield assembly to obviate the danger of a handler thereof being accidentally pricked by the point of the needle after it has been injected in a patient and then withdrawn, the withdrawn needle possibly being contaminated with infectious microorganisms. The assembly includes a needle-supporting hub receivable in a socket formed at the front end of a fluid chamber in a standard syringe provided with a projecting nozzle which is inserted in the hollow base of the hub to communicate with the needle. Anchored on top of the hub which serves as a pedestal therefor and surrounding the needle is a helical spring, the convolutions in the upper section of the spring forming a cone and terminating in a shield through whose center passes the axis of the helix. The normal length of the spring is such as to place the shield in the protective mode of the assembly in front of the needle point to prevent human contact therewith.

7 Claims, 5 Drawing Sheets

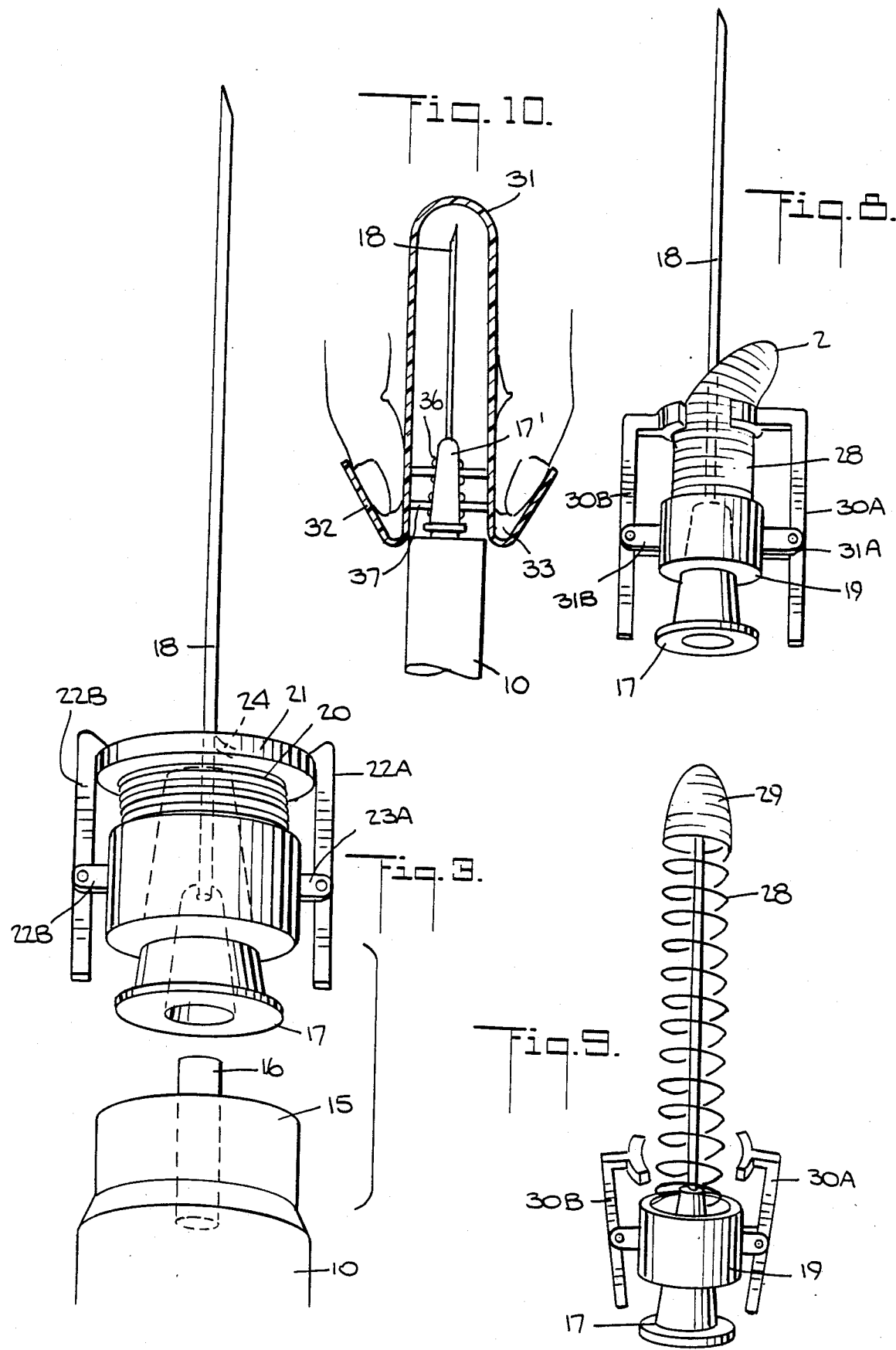

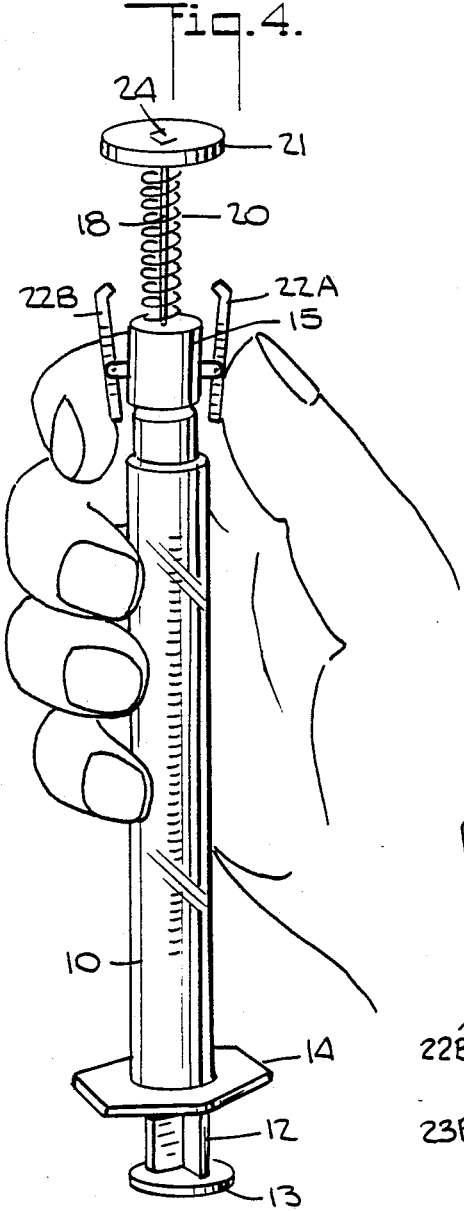
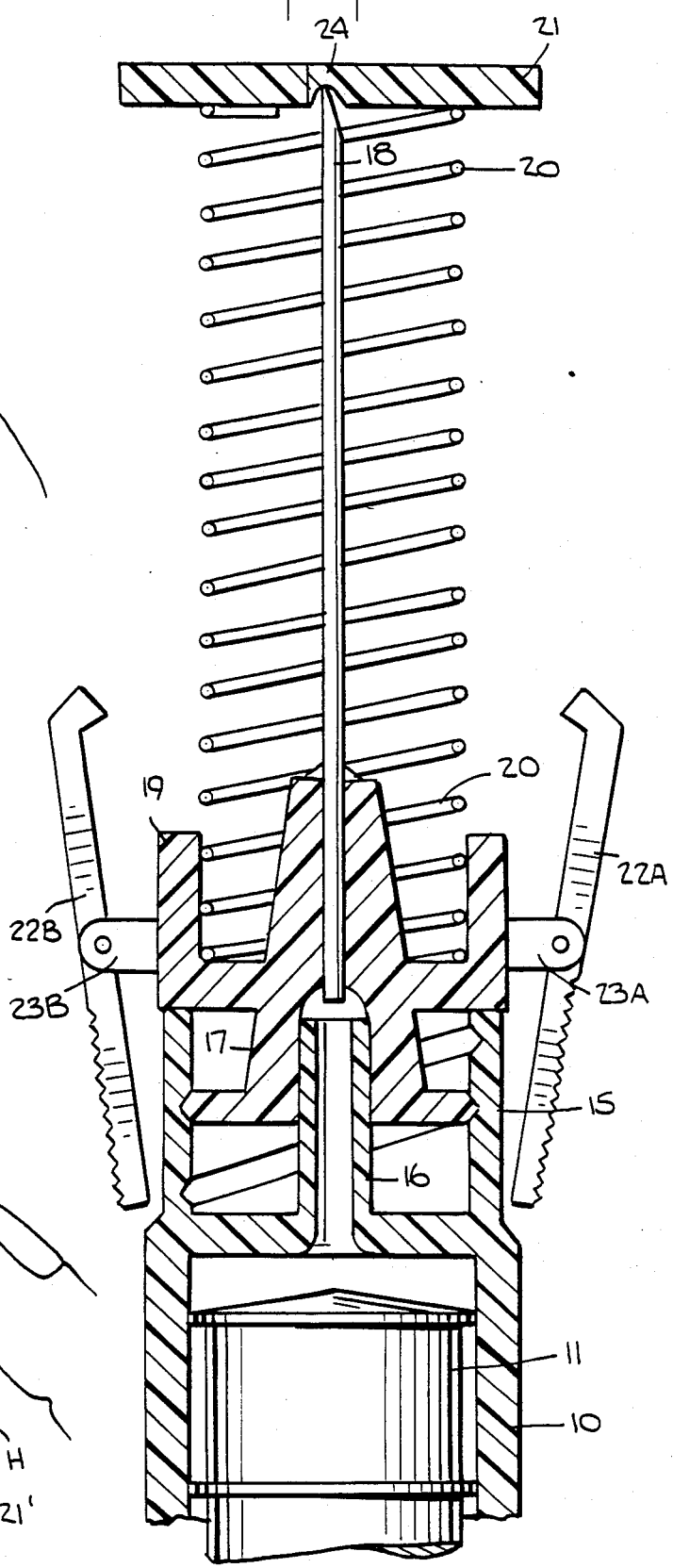
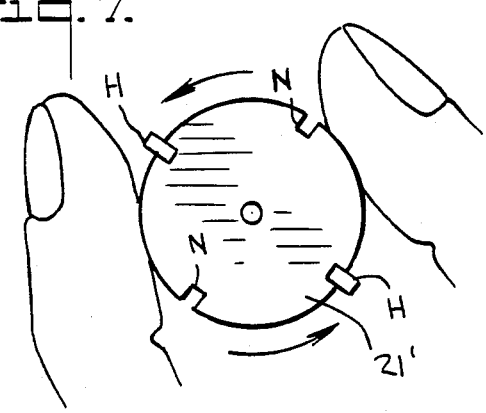

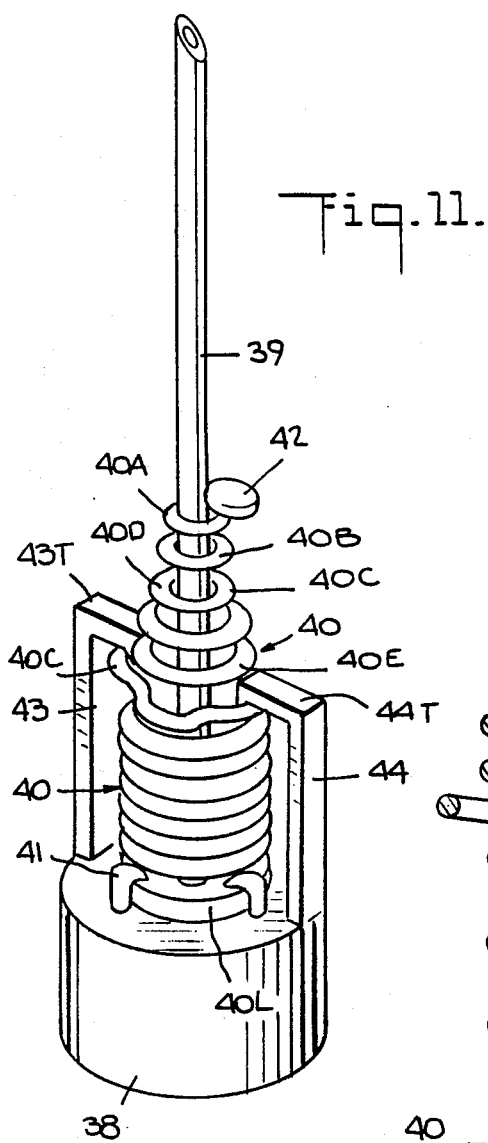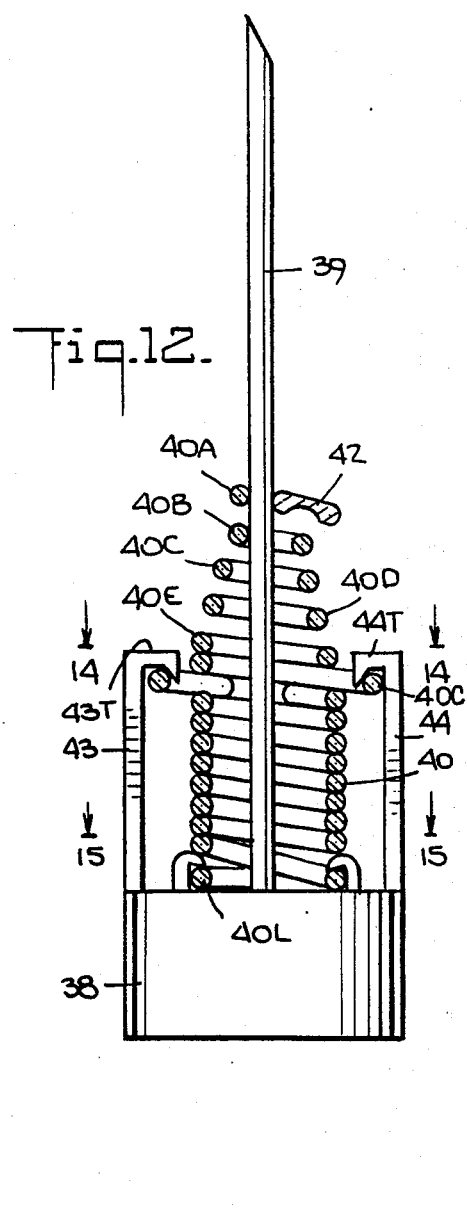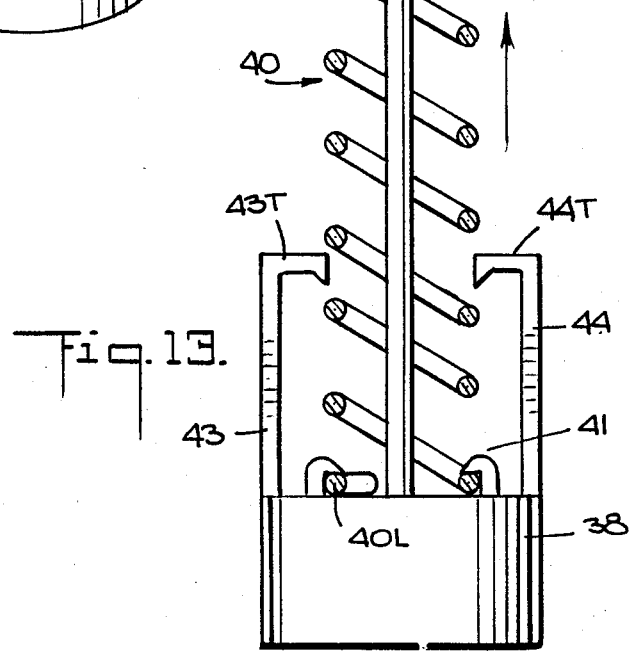

SAFETY HYPODERMIC NEEDLE SYRINGE

RELATED APPLICATION

This application is a continuation-in-part of our copending application Ser. No. 235,466, filed Aug. 24, 1988, now U.S. Pat. No. 4,863,435 entitled SAFETY HYPODERMIC SYRINGE.

BACKGROUND OF INVENTION

1. Field of Invention

This invention relates generally to hypodermic syringes, and in particular to a safety hypodermic needle and shield assembly for a hypodermic needle to permit its use, the assembly when unlatched assuming an extended mode in which the shield protectively covers the point of the needle to prevent accidental sticks thereby.

2. Status of Prior Art

A hypodermic needle is usable for intravenous, subcutaneous and intramuscular injection of fluids, or the removal of blood (venipuncture), body fluids or abnormal collections thereof, the needle being of hollow construction and having a slanted open point. When the needle is mounted on a syringe, it is adapted to aspirate or inject fluids for diagnostic or therapeutic purposes.

Disposable hypodermic needles are now mass produced at low cost, many billions of such syringes being used every year in the health care field. While the modern hypodermic syringe now includes a fluid chamber molded of synthetic plastic material appliance remains much as it was in 1853 when it was invented by Charles Pravaz, a French physician.

In a hypodermic syringe of standard design, a piston is slidable within a cylindrical fluid chamber, the shank of the piston extending beyond the open rear end of the cylinder and terminating in a handle. The front end of the chamber is provided with a projecting nozzle that is coaxial with an internally-threaded socket adapted to receive a needle-supporting hub. When the hub is screwed into the socket, the nozzle is then received therein to communicate with the needle.

A hypodermic needle and a syringe attached thereto are distributed in sterile condition within a plastic bubble package and to protect them against contamination in storage and shipment. In addition, the needle is enclosed in a removable overcap whose inlet end snaps onto the needle hub. Thus, after the hypodermic needle and syringe are removed from its package, in order to put it to use one must first remove the overcap to expose the needle. After the hypodermic syringe has been injected into a patient and then withdrawn, it is the usual practice before discarding the syringe to place the overcap back on the needle hub so that those thereafter handling discarded syringes for purposes of disposal will not be pricked thereby.

When a sterile hypodermic needle is injected into a patient suffering from hepatitis or other infectious disease, when the needle is then withdrawn from the patient, it may be contaminated with infectious agents. Hence, should the handler inadvertently prick himself with this contaminated needle, the consequences may be serious.

The possibility of accidental contamination by needle puncture of the skin of those individuals in the health care field who employ hypodermic syringes for venipuncture, the withdrawal of body fluids or for any other medical purpose is fairly high and represents a significant risk. Thus, physicians, nurses, laboratory personnel, paramedics and other involved in the care and treatment of patients are in danger of being accidentally inoculated with infectious microorganisms by contaminated needles.

Most accidental needle sticks occur when the needles are being recapped; for to do so properly, one must first align the needle with the relatively small diameter inlet of the overcap. Should the needle be misaligned, as may well happen should the handler be careless, distracted or fatigued, the point of the needle will not enter the overcap but may instead puncture the finger of the handler.

It is well established that in the last 25 years the risks involved in handling hypodermic syringes has markedly increased. Statistics indicate very high rates of hepatitis B infection among medical and laboratory personnel by reason of this accidental mode of disease transmission. The results of positive hepatitis surface antigen testing reveals a five-to-fifteen fold increase in the risk of developing the antigen and antibody (as well as chronic hepatitis) among surgeons and other health care personnel dealing with patients belonging to high risk groups, such as patients undergoing renal dialysis, drug addicts, and the like. In a recent issue of the newsletter, Biomedical Business International, it is reported that there are between 800,000 and one million accidental needle sticks each year.

Medical personnel who care for patients suffering from AIDS run a still higher risk; for a needle contaminated with Should the handler of this needle be accidentally punctured, he faces the prospect of contracting a disease currently having a 100% mortality rate as compared, say, to the 5 to 10% mortality rate for hepatitis B.

Yet, in the prior art, it was only in recent years that patents have issued dealing with expedients to prevent accidental needle sticks. Thus, the expired patents to Bauer, U.S. Pat. No. 2,674,246; White, U.S. Pat. No. 2,876,770; Saenz, U.S. Pat. No. 3,046,985; and Armao, U.S. Pat. No. 3,134,380, through dealing with hypodermic syringes are mainly concerned with the fact that most patients are frightened by the mere appearance of a hypodermic syringe. Patients object to being punctured by a sharp needle, even though it is a relatively painless experience. To overcome this fear, these patents provide a guard to conceal the needle so that it is never seen by the patient, even as he is being injected. Thus, the White patent provides a spring-biased guard which normally covers the needle. But when the needle is injected in a patient, the nose of the guard presses against the tissue and the spring is compressed to permit the needle to project out of the guard into the tissue.

The 1988 patent to Wanderer et al., U.S. Pat. No. 4,731,059, is concerned with preventing needle sticks, and for this purpose provides a shield which is slidable from a position covering the needle to a position overlying the fluid chamber so that the needle can be exposed when put to use and thereafter shielded. A somewhat similar arrangement is disclosed in the 1987 patent to Fox, U.S. Pat. No. 4,695,274, which shows a retractable safety jacket for a hypodermic needle.

One practical problem with the safety shields or needle guards of the type disclosed in the Wander et al. and Fox patents is that when the needle is exposed so that the syringe can be put to use, the retracted guard then covers and obscures the transparent chamber which is graduated so that one can determine the amount of fluid that is contained therein. Hence this guard interferes with the proper operation of the hypodermic syringe.

But the more serious drawbacks of prior art needle guard arrangements is that they require a modification of the basic configuration of the standard hypodermic syringe to accommodate the guard. Thus in one commercially-available form of safety hypodermic syringe, in order to accommodate a needle guard, the needle is mounted on an elongated extension rod projecting from the fluid chamber, so that when the guard is retracted it overlies the extension rod, not the fluid chamber. Hence, fluid from the chamber must be conducted through the extension rod which by its very nature elongates the hypodermic syringe, making it more difficult to handle. Also, the extension tube will retain and waste an excessive amount of fluid.

Also of prior art interest are the patents to Strauss, U.S. Pat. No. 4,664,654, and Karczmer, U.S. Pat. No. 4,795,432.

SUMMARY OF INVENTION

In view of the foregoing, the main object of this invention is to provide a safety hypodermic needle and shield assembly for a syringe which obviates the danger of a handler thereof being accidentally pricked by the point of the needle after it has been injected in a patient and then withdrawn.

More particularly, an object of this invention is to provide a safety hypodermic needle and shield assembly of the above type which requires no basic modification of the design of a standard syringe and which can be manufactured inexpensively on a mass production basis.

Also an object of the invention is to provide an assembly of the above type which can readily be coupled to the fluid chamber of a standard hypodermic syringe.

Briefly stated, these objects are attained in a hypodermic syringe provided with a safety hypodermic needle and shield assembly to obviate the danger of a handler thereof being accidentally pricked by the point of the needle after it has been injected in a patient and then withdrawn, the withdrawn needle possibly being contaminated with infectious microorganisms. The assembly includes a needle-supporting hub receivable in a socket formed at the front end of a fluid chamber in a standard syringe provided with a projecting nozzle which is inserted in the hollow base of the hub to communicate with the needle. Anchored on top of the hub which serves as a pedestal therefor and surrounding the needle is a helical spring, the convolutions in the upper section of the spring forming a cone and terminating in a shield through whose center passes the axis of the helix. The normal length of the spring is such as to place the shield in the protective mode of the assembly in front of the needle point to prevent human contact therewith. Below the upper section is a control convolution having four outwardly extending lobes whose peaks are spaced 90 degrees apart. When the assembly is in its retracted mode in which the spring is compressed and the shield is canted to allow the needle to pass through the spring, two of the lobes are engaged by a pair of diametrically-opposed latching elements mounted on the pedestal, thereby exposing the needle to permit its injection in a patient. After the needle is withdrawn, the handler returns the assembly to its protective mode by grasping the other two lobes to twist the control convolution to effect disengagement of the latching elements.

BRIEF DESCRIPTION OF DRAWINGS

For a better understanding of the invention as well as other objects and further features thereof, reference is made to the following detailed description to be read in conjunction with the accompanying drawings, wherein:

FIG. 4 shows the assembly in the hands of a user who has unlatched it to cause the assembly to assume its extended mode;

FIG. 5 is a section taken through the assembly in its extended mode;

FIG. 6 illustrates a second preferred embodiment of an assembly which is shown in its retracted mode;

FIG. 7 is a top view of the shield included in the FIG. 6 assembly;

FIG. 8 illustrates a third preferred embodiment of an assembly which is shown in its retracted mode;

FIG. 9 shows this assembly in its extended mode;

FIG. 10 illustrates an improved overcap in accordance with the invention;

FIG. 11 is a perspective view of a fourth preferred embodiment of an assembly in accordance with the invention, shown in its retracted mode;

FIG. 12 is a side view of the assembly shown in its retracted mode;

FIG. 13 is a side view of the assembly shown in its protective or extended mode;

DETAILED DESCRIPTION OF INVENTION

First Embodiment

Figure 1:
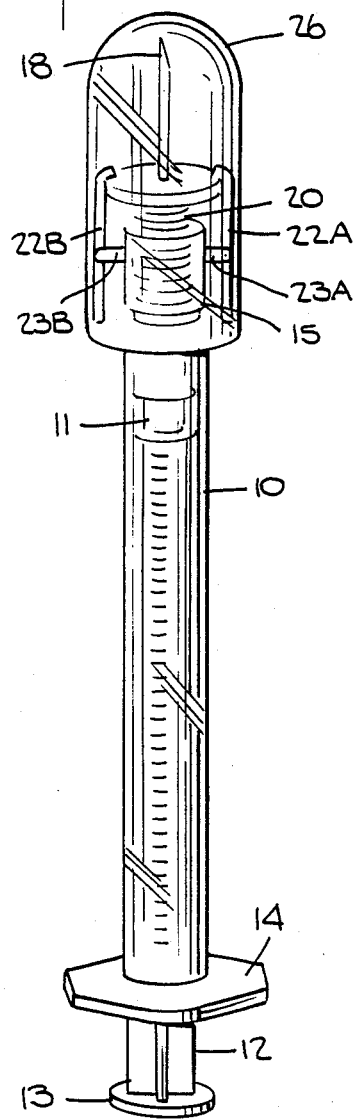
FIG. 1 illustrates, in perspective, a hypodermic syringe provided with one preferred embodiment of a safety hypodermic needle and shield assembly in accordance with the invention, the assembly being shown in its retracted mode.
Figure 2:
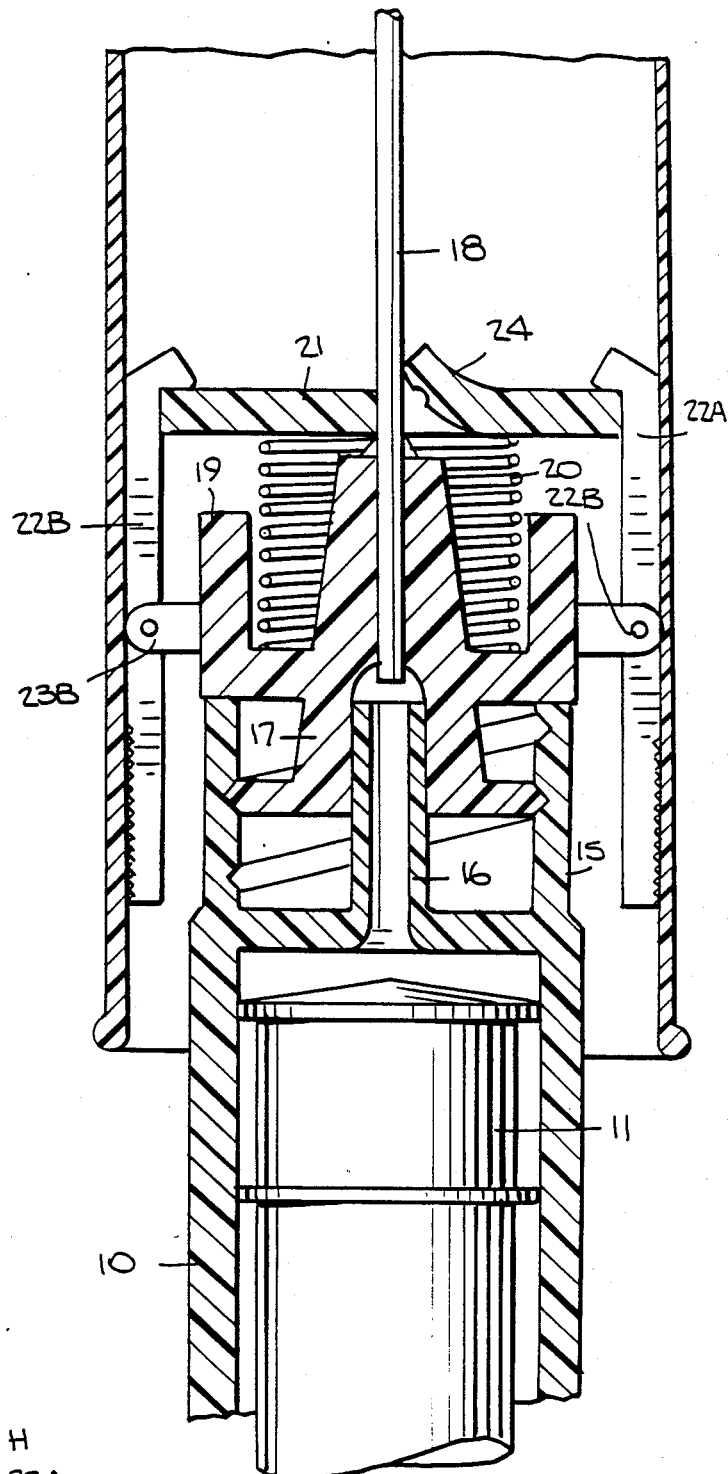
FIG. 2 is an enlarged sectional view of the retracted assembly.
Figure 3:
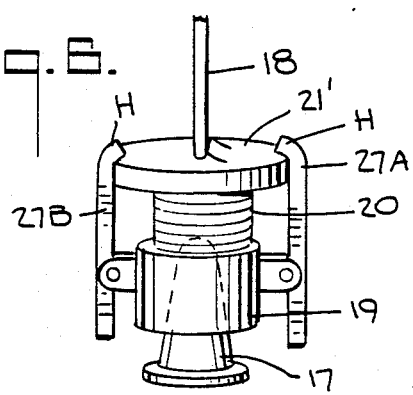
FIG. 3 is an enlarged perspective view of the assembly in its retracted mode and of the socket of the fluid chamber to which the assembly is coupled.

Referring now to FIGS. 1 to 3 of this drawing, shown therein is a hypodermic syringe provided with a safety hypodermic needle and shield assembly in accordance with the invention. The assembly in its retracted mode, which is the mode shown in FIGS. 1 to 3, exposes the hypodermic needle to permit its injection into a patient. In its extended mode, the assembly acts to shield the point of the needle to prevent an accidental stick.

Included in the syringe is a cylindrical fluid chamber 10 formed of transparent, synthetic plastic material such as polyethylene, polypropylene, polystyrene or PVC having indicia thereon to indicate the level of fluid in the chamber. Slidable within the chamber is a piston 11 for ejecting fluid from the chamber or drawing fluid therein, the piston having a shank 12 which extends beyond the open end of the chamber and terminates in a handle 13.

As is conventional, the rear end of chamber 10 is provided with a flange 14 so that to manipulate the piston to draw fluid from a patient or to inject fluid into the patient, the user holds the flange with the fingers of one hand while grasping handle 13 with fingers of the other hand.

At the front end of chamber 10 is an internally-threaded cylindrical socket 15 and coaxially disposed therein is a nozzle 16 whose inlet communicates with the interior of the chamber. Threadably received in socket 15 is a tapered needle-supporting hub 17, nozzle 16 entering the hollow base section of the hub to communicate with a hypodermic needle 18 supported at the apex of the hub.

Integral with hub 17 is a cup-shaped pedestal 19 which when the base section of the hub is screwed into socket 15 is then seated on the rim thereof to provide a stable support for the needle and for a compressible helical spring 20 which surrounds needle 18. Spring 20, which is preferably formed of stainless steel, is anchored at its lower end on pedestal 19, the upper end of the spring supporting a disc-shaped shield 21 whose diameter is greater than that of the pedestal. Shield 21 is provided with a center bore to permit the needle to pass therethrough. In practice, the shield, the pedestal and the disc and all other elements of the assembly other than the spring and needle are molded of a suitable synthetic plastic such as polypropylene.

In the retracted mode of the assembly, spring 20 is retracted position adjacent the apex of hub 17 to maintain the spring in its compressed state. The latching mechanism for this purpose in the first embodiment is constituted by a pair of toggles 22A and 22B hingedly mounted at diametrically-opposed positions on brackets 23A and 23B integral with the cylindrical shell of the cup-shaped pedestal 19. The hinges for this purpose are preferably in the form of torsion bars integral with brackets 23A and 23B, although other forms of spring-biased hinges may be used for the toggles. The upper end of the toggles are hook-shaped to engage shield 21.

Shield 21 is provided with a trap door 24 to shut the bore therein in the extended mode of the assembly when the latching mechanism is released and the disc is then raised by spring 20 to a position just above the point of the needle. In the embodiment shown, trap door 24 is in the form of a flexible flap having a recess 25 at its underside to receive the point of the needle when the trap door is shut. In practice, instead of a deflectable flap, the trap door may be slidable and supported by crossed flexible bars to permit its retraction relative to the bore.

The assembly includes an overcap 26 of synthetic plastic material having a diameter which permits the overcap to frictionally engage toggles 22A and 22B in their vertical latching state, as shown in FIG. 1. Hence the overcap acts not only to enclose and protect the needle but also to ensure that the assembly is maintained in its retracted mode during shipment and storage. Because the overcap houses the entire assembly, it is a simple matter, by holding the overcap, to then screw the assembly onto the socket of the fluid chamber.

In practice, therefore, the capped assembly may be separately packaged, and used in conjunction with syringes of various sizes, as long as these syringes include a fluid chamber socket adapted to receive the hub of the safety needle and shield assembly. The assembly itself may be made with needles of different gauges and in different dimensions appropriate to the syringes to which the assemblies are to be coupled.

When the hypodermic syringe in accordance with the invention is to be used, overcap 26 is removed to expose needle 18 of the retracted safety shield assembly, and the patient is then injected with the needle. After the needle is withdrawn from the patient, the individual who is holding the syringe in his hand then uses his fingers, as shown in FIGS. 4 and 5, to operate toggles 22A and 22B to release shield 21 which is then raised by spring 20 to a position just above the point of the needle, thereby protecting the individual from being pricked by the point of the needle. It is no longer necessary, as with conventional hypodermic syringes, to place the overcap back on the syringe, although one may do so.

Second Embodiment

In the safety shield assembly shown in FIGS. 6 and 7, instead of spring-biased toggles as in the first embodiment, the shield 21' supported at the upper end of helical spring 20 is held in its retracted position by a pair of fixed latching arms 27A and 27B which are integral with cup-shaped pedestal 19, the arms having hooks H at their upper ends which engage the disc-shaped shield.

Shield 21' is provided with a pair of diametrically opposed notches N, so that by turning the shield to an angular position at which the notches register with hooks H, the hooks fall into these notches and the shield is then released from the latching arms to permit the assembly to assume its extended mode. In all other respects, the assembly functions in the same manner as in the first embodiment.

Third Embodiment

In the embodiment shown in FIGS. 8 and 9, spring 28 surrounding needle 18, instead of terminating in a separate shield, as in the prior embodiments, is so convoluted at its upper end as to create a coiled conical shield 29 in which the convolutions are of progressively smaller diameter.

In its retracted mode, as shown in FIG. 8, spring 28 is compressed, needle 18 going through the space between adjacent convolutions at the base of conical shield 29, so that the conical shield is now offset with respect to the needle. The toggles 30A and 30B hingedly supported on brackets 31A and 31B secured at diametrically-opposed positions on pedestal 19. The upper ends of the toggles are provided with arcuate shoes S to engage the spring and maintain it in its compressed state. When these toggles are operated by the fingers of the handler as shown in FIG. 9, the spring is released to cause shield 29 to assume a protective position just above the point of the needle, this being the extended mode of the assembly.

While there have been shown and described preferred embodiments of a safety hypodermic syringe in accordance with the invention, it will be appreciated that many changes and modifications may be made therein without, however, departing from the essential spirit thereof.

Improved Overcap

As pointed out previously, most accidental needle sticks occur when a hypodermic needle, after being withdrawn from a patient is being recapped. Because the inlet of the conventional overcap is of relatively small diameter, the user may have difficulty in aligning the point of the needle with the inlet, and a misaligned needle instead of entering the inlet may puncture a finger of the handler.

Overcap 26 shown in FIG. 1 is of relatively enlarged diameter, and to this degree reduces the possibility of accidental sticks. It is also known to provide a safety needle sheath or overcap having a funnel-shaped receiving end (see Pedicano et al. U.S. Pat. No.

4,610,667). But an overcap of this design does not fully protect the fingers of the user.

In the overcap 31 shown in FIG. 10, the diameter of this sheath is about the same as the diameter of the cylindrical chamber 10 of the syringe, and is therefore much greater than the diameter of a conventional overcap. The inlet end 31A of overcap 31 is outwardly flared and cured to provide a radiused entry which is integral with a frusto-conical gauntlet 32. This gauntlet defines an annular pocket 33 for receiving fingers 34 of the user. Gauntlet 33 may be buttressed by internal ribs at diametrically opposed positions extending between the inner wall of the gauntlet and the outer wall of the overcap.

The hub 17' on which needle 18 is mounted is so molded as to form detents 36 on its exterior wall. These detents are engaged by flexible fingers 37 that are molded on the inner wall of the overcap. The relationship of the flexible fingers to the detents is such as to provide a frictional fit, the fingers flexing to permit the overcap to be fitted onto the hub or withdrawn therefrom. Or the detents may be angled relative to the flexible fingers to permit a screw-like action for fitting the overcap onto the hub or for withdrawing it from the hub.

Hence the gauntlet acts as a protective shield for the user's fingers, while the oversize receiving end of the overcap with its radiused inlet greatly reduces the possibility of the needle failing to enter the overcap, even when this operation is carried out carelessly. In practice, the portion of the overcap beyond the finger pressure point may be reduced in diameter to about the diameter of the existing overcap which is just sufficient to protect the needle, thereby effecting a substantial saving in material.

Fourth Embodiment

Referring now to FIGS. 11 to 15, there is shown another embodiment of a safety hypodermic needle and shield assembly in accordance with the invention to obviate the danger of a handler thereof being accidentally pricked by the point of the needle after it has been injected in a patient and then withdrawn.

This embodiment includes a hub 38 for supporting a hypodermic needle 39 in the same manner as in the previous embodiments, the hub having a hollow base which receives the nozzle of a standard syringe so that fluid from the chamber of the syringe may be fed into the needle or fluid from the needle may be conducted into the chamber. The hub screws into an internally threaded socket at the end of the fluid chamber concentric with the nozzle, as in the previous embodiments.

The top of hub 38 serves as a pedestal for a helical spring 40 which surrounds needle 39. The lowermost convolution 40L of the spring is secured to the top of hub 28 by four lugs 41, as best seen in FIG. 5. The convolutions 40A to 40E which together form the upper section of the spring are of progressively increasing diameter to define a cone, the uppermost convolution 40A terminating in a disc-shaped shield 42.

The normal length of spring 40, as best seen in FIG. 13, is such as to place shield 42 in front of the point of needle 39 to prevent human contact with the needle, this being the protective or extended mode of the assembly. In this mode, axis X of the spring helix passes through the center of the shield.

Figure 14:
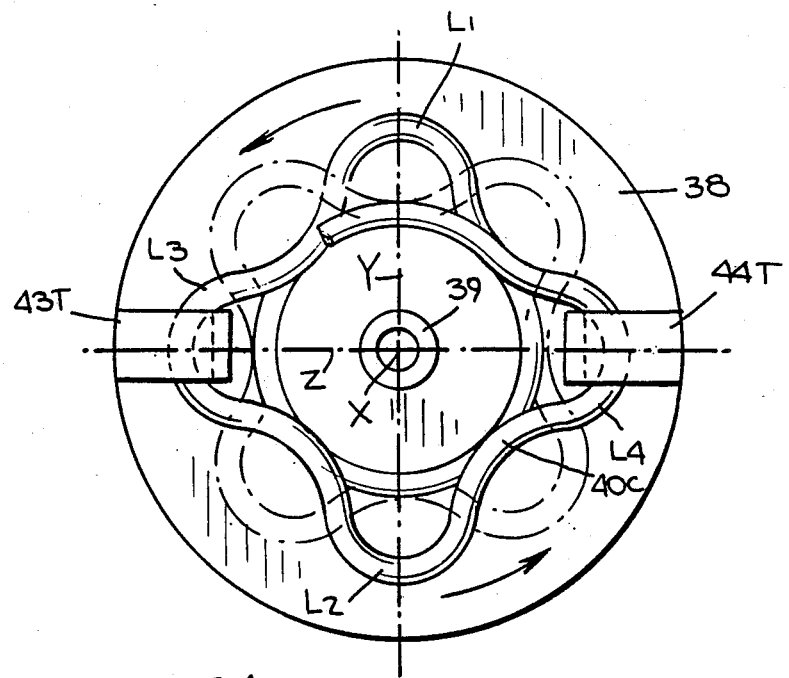
FIG. 14 is a top view taken in plane 14—14 in FIG. 12.
Figure 15:
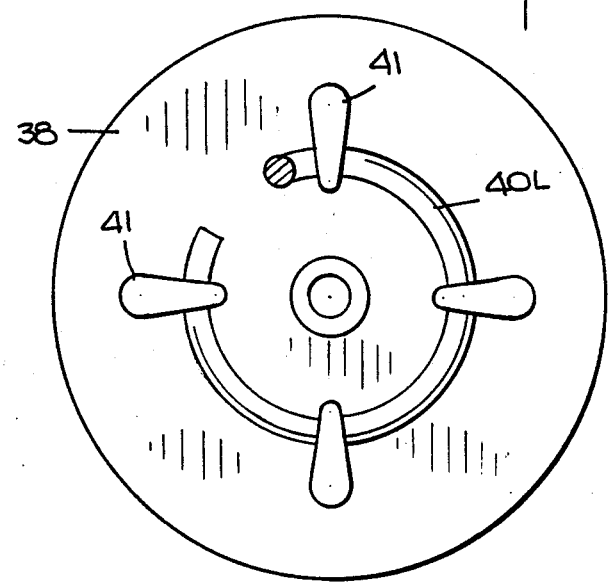
FIG. 15 is a top view taken in the plane 15—15 in FIG. 12.

Below the upper section of spring 40 is a control convolution 40C which, as best seen in FIG. 14, is so deformed as to create four outwardly extending lobes $L_1$, $L_2$, $L_3$ and $L_4$ whose peaks are spaced 90 degrees apart, so that lobes $L_1$ and $L_2$ are at diametrically opposed positions on an axis Y normal to the longitudinal helix axis X, and lobes $L_3$ and $L_4$ are at diametrically opposed positions on an axis Z normal to axis X and at right angles to axis Y.

Integral with hub 38 and extending upwardly therefrom at diametrically-opposed positions to engage lobes $L_3$ and $L_4$ is a pair of rigid latching elements 43 and 44, each having at its upper end an inwardly directed holding tab (43T and 44T).

In the retracted mode of the assembly, as shown in FIGS. 11 and 12, spring 40 is compressed, and to allow hypodermic needle 39 to pass through the spring and to be exposed for injection into a patient, shield, 42 on the topmost convolution 40A is then displaced to one side. The spring is held in its compressed state by latching elements 43 and 44 whose tabs 43T and 44T then engage lobes $L_3$ and $L_4$ of control convolution 40C, as best seen in FIG. 14.

After the patient has been injected with the needle by the handler and the needle is withdrawn, then before putting on the overcap as in the previous embodiments, the assembly which is in its retracted mode must now be converted to its protective or extended mode. To this end, the handler simply grasps lobes $L_1$ and $L_2$ of the control convolution and twists it a few degrees to effect disengagement of lobes $L_3$ and $L_4$ from latching elements 43 and 44, thereby permitting the spring to expand to place shield 42 in front of the needle point.

It is now safe to fit the overcap over the assembly; for no matter how carelessly this is done, the handler runs no risk of pricking himself with the needle, for the needle point is now shielded.

While there have been shown and described various embodiments of a safety hypodermic needle and shield assembly, all of which can be associated with a standard syringe, it will be appreciated that many changes may be made therein within the spirit of the invention as defined in the claims.

In the first embodiment of the invention as shown in FIG. 3, the helical spring has convolutions of uniform diameter, and when the spring is fully compressed, the shield at its end is then latched by a pair of toggles, this being the retracted mode of the assembly. In an alternative embodiment, the spring is composed of an upper section whose convolutions are of reduced diameter relative to those of a lower spring section to define a shoulder at the junction between the sections. It is this shoulder and not the shield which is engaged by the latching toggles in the retracted mode. In this alternative embodiment, the shield need not have a central hole and a trap door as in FIG. 3, so that the needle can pass therethrough, but can be displaceable as in FIG. 11 of the fourth embodiment.

We claim:

1. In combination with a standard syringe whose fluid chamber has a piston slidable therein and is provided at its front end with a projecting nozzle and a cylindrical, internally-threaded socket concentric therewith; a safety hypodermic needle and shield assembly adapted to prevent accidental stick by the point of the needle after the needle has been injected into a patient and then withdrawn, said assembly comprising:

(a) a hub to support the needle provided with a hollow base threadably receivable in the socket of the syringe whereby the nozzle is then inserted in the hollow base to communicate with the needle to conduct fluid from the chamber into the needle or to conduct fluid from the needle into the chamber;

(b) a compressible helical spring anchored on top of the hub which serves as a pedestal therefor and surrounding the needle;

(c) a shield supported at the upper end of the spring whose normal length is such as to place the shield protectively in front of the point of the needle, said shield being capable of permitting compression of the spring and the exposure of the needle; and (d) releasable latching means supported on the pedestal which in a retracted mode of the assembly when the spring is compressed and the shield is retracted to hold the spring in its compressed state at which the needle is exposed for use, and in an extended mode of the assembly when the spring is released, to cause the shield to assume its place in front of the point to prevent accidental stick.

2. The combination as set forth in claim 1, wherein the lowermost convolution of the spring is held by lugs to the top of the hub.

3. The combination as set forth in claim 1, wherein said shield is attached to the uppermost convolution of the spring and when the spring is compressed is displaced to permit exposure of the needle.

4. The combination as set forth in claim 3, in which the convolutions in the upper section of the spring beginning with the uppermost convolution are of progressively increasing diameter to form a cone in which the point of the needle is received.

5. The combination as set forth in claim 4, wherein the convolution below the upper section is a control convolution which is engaged by the latching means.

6. The combination as set forth in claim 5, wherein said control convolution is deformed to provide two pairs of outwardly extending lobes at diametrically opposed positions, the lobes of one pair being engaged by the latching means, the lobes of the other pair acting as a handle permitting the handler to twist the control convolution to effect disengagement of the latching means.

7. The combination as set forth in claim 6, wherein said latching means is constituted by a pair of latching elements extending upwardly from the pedestal and provided at their ends with inwardly extending tabs to engage the lobes of said one pair.

* * * * *